United States Patent [19]

Enomoto et al.

[11] Patent Number: 4,780,081

[45] Date of Patent: Oct. 25, 1988

[54] ARTIFICIAL DENTAL ROOT CAPABLE OF BEING FIRMLY FIXED TO A JAWBONE

[75] Inventors: Hiroaki Enomoto, Niigata; Masahiro Yoshida, Tokyo, both of Japan

[73] Assignee: Hoya Corporation, Tokyo, Japan

[21] Appl. No.: 3,196

[22] Filed: Jan. 14, 1987

[30] Foreign Application Priority Data

Jan. 14, 1986 [JP] Japan .................................... 61-4140
Jan. 14, 1986 [JP] Japan .................................... 61-4141

[51] Int. Cl.$^4$ .............................................. A61C 8/00
[52] U.S. Cl. .................................................. 433/174
[58] Field of Search ................................ 433/173, 174

[56] References Cited

U.S. PATENT DOCUMENTS

| | | | |
|---|---|---|---|
| 3,579,831 | 3/1969 | Stevens | 433/174 |
| 4,103,422 | 8/1978 | Weiss et al. | 433/174 |
| 4,229,169 | 10/1980 | Smith | 433/176 |
| 4,406,623 | 9/1983 | Grafelmann et al. | 433/174 |

*Primary Examiner*—Robert Peshock
*Attorney, Agent, or Firm*—Roberts, Spiecens & Cohen

[57] ABSTRACT

In an artificial dental root having a first end, a second end which is opposite to the first end and which is to be embedded into a jawbone, and a shank between the first and the second ends, a thread portion is formed on the shank and has a pitch which is not smaller than 2 millimeters. The pitch is preferably between 3 and 4 millimeters. The thread portion comprises a screw thread which has the above-mentioned pitch, a width, and a height. At least one of the width and the height of the screw thread is reduced in a direction of the second end. A rotation stopper member is formed on the second end and may be a groove and/or a projection. The shank may be reduced in diameter as it is near to the second end.

12 Claims, 2 Drawing Sheets

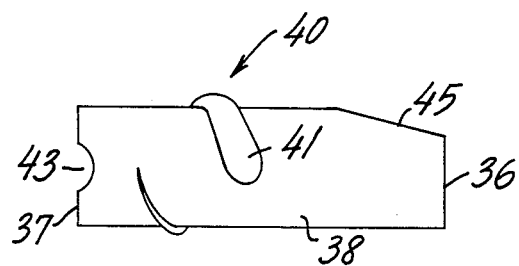
FIG. 5
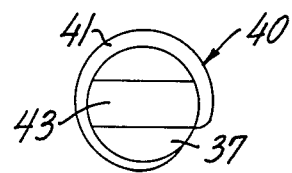
FIG. 6
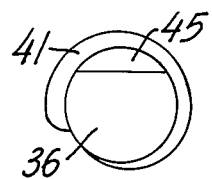
FIG. 7
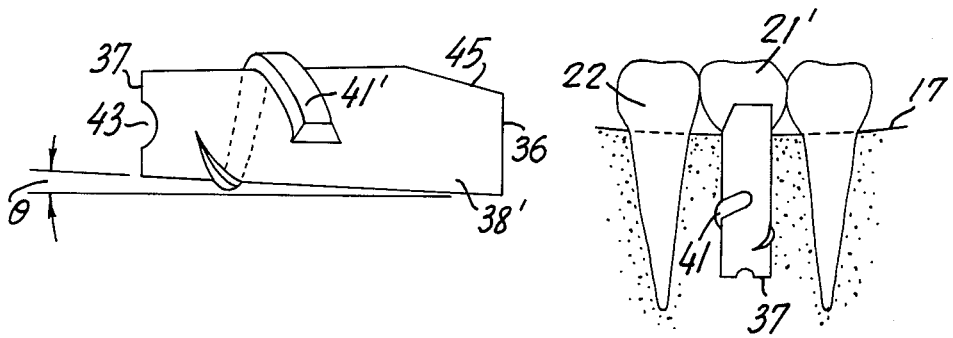
FIG. 8
FIG. 9

ARTIFICIAL DENTAL ROOT CAPABLE OF BEING FIRMLY FIXED TO A JAWBONE

BACKGROUND OF THE INVENTION

This invention relates to an artificial dental root for use in dental implantation which is carried out after detachment or evulsion of a natural tooth.

A natural tooth is important for mastication and is supported through a peridentium and a gum in a tooth socket, namely, dental alveoli, of a jawbone, such as a maxilla or mandible. Extraction of the natural tooth leaves a hole in the tooth socket. Such a hole is gradually filled with an os novum with time. However, undesirable involution or degradation of the jawbone is progressive at an edge of the hole when the hole is left as it is.

Dental implantation is useful for alleviation of undesirable involution or degradation of the jawbone and is carried out by implanting an artificial dental root into the jawbone, specifically, alveolar bone. Such an artificial dental root must be formed by a material which is non-toxic to humans.

Under the circumstances, a proposal has been made regarding artificial dental roots of polycrystalline alumina and apatite. Such conventional artificial dental roots are embedded into the jawbone by surgical operation. However, the probability of success is very low in the surgical operation for implantation of the conventional artificial dental roots. In other words, failure often occurs in the surgical operation. This impedes the wide use of the surgical operation for implantation. Such low probability of success in the surgical operation results from difficulty of initial fixation of the conventional artificial dental roots.

SUMMARY OF THE INVENTION

It is an object of this invention to provide an artificial dental root which can readily be implanted into a jawbone without a difficult surgical operation.

It is another object of this invention to provide an artificial dental root of the type described, which is snugly and strongly fixed to the jawbone on initial fixation.

It is a further object of this invention to provide an artificial dental root of the type described, which can avoid involution or degradation of the jawbone.

According to this invention, an artificial dental root has a first end, a second end opposite to said first end, a shank between the first and the second ends, and a thread portion which is formed on the shank and which has a pitch not smaller than 2 millimeters.

BRIEF DESCRIPTION OF THE DRAWING

FIG. 5 shows an elevational view of an artificial dental root according to a first embodiment of this invention;

FIG. 6 shows a side view of the artificial dental root illustrated in FIG. 5;

FIG. 7 shows another side view of the artificial dental root illustrated in FIG. 5;

FIG. 8 shows an elevational view of an artificial dental root according to a second embodiment of this invention; and FIG. 9 shows a view for use in describing the artificial dental root which is illustrated in FIG. 5 and which is embedded into a jawbone.

DESCRIPTION OF THE PREFERRED EMBODIMENTS

Figure 1:
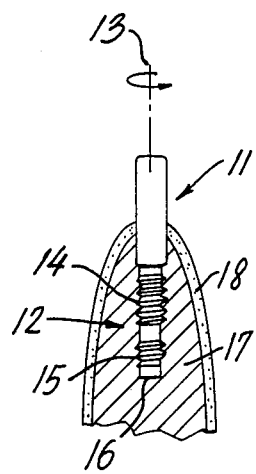
FIG. 1 shows a view of a conventional artificial dental root embedded into a jawbone through a gum with the jawbone and the gum sectioned.

Referring to FIG. 1, a conventional artificial dental root will be described for a better understanding of this invention and is composed of alumina. The illustrated artificial dental root has a first rod portion 11 and a second rod portion 12 connected to the first rod portion 11. The first and the second rod portions 11 and 12 are linear along an axis 13. The first rod portion 11 provides a first end directed upwards of FIG. 1 while the second rod portion 12 provides a second end directed downwards. The second rod portion 12 comprises a cylindrical rod which has a reduced diameter in comparison with a diameter of the first rod portion 11. First and second screw threads 14 and 15 are formed around the cylindrical rod and spaced apart from each other on the cylindrical rod. Each of the first and the second screw threads 14 and 15 has a uniform pitch less than 1 millimeter.

When the artificial dental root is implanted, a hole 16 is formed on a jawbone 17 (precisely, an alveolar bone) through gum 18, as symbolized by a thick line at the second end of the artificial dental root. In this event, the gum 18 is partially cut to expose the jawbone 17. Subsequently, the artificial dental root is screwed into the hole 16 with the second rod portion 12 directed downwards and with the first rod portion 11 partially exposed to an outside of the gum 18.

Thus, the artificial dental root is mechanically fixed to the jawbone 17 by embedding the second rod portion 12 into the jawbone 17. Such an artificial dental root of alumina is excellent in biocompatibility. However, no assimilation takes place between alumina and the jawbone 17. The artificial dental root is therefore never adhered to the jawbone 17. This means that no clearance is permissible between the jawbone 17 and the artificial dental root. If any clearance is left between the jawbone 17 and the artificial dental root, the artificial dental root is loosened and detached from the jawbone 17.

In addition, the illustrated artificial dental root might be rotated after it is received into the hole 16. Such rotation of the artificial dental root might result in breakage of screw threads formed in the jawbone 17 because the hardness of the jawbone 17 varies as high as wood, although the hardness of the jawbone 17 is according to age, anamnesis, and the constitution of the individual.

According to the inventors' experimental studies, it has been found that breakage of the screw threads in the jawbone 17 is liable to frequently occur as the pitch of the screw threads 14 and 15 becomes small.

Figure 2:
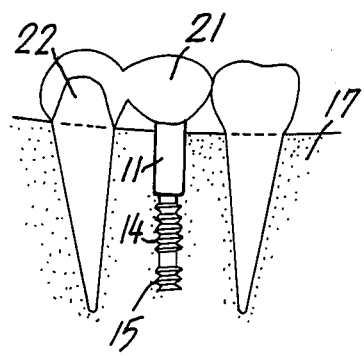
FIG. 2 shows a view of the conventional artificial dental root which is covered with an artificial crown of tooth and which is embedded into the jawbone.

Referring to FIG. 2 together with FIG. 1, an artificial crown 21 of tooth shape is supported on the artificial dental root of alumina illustrated in FIG. 1. In this event, the artificial crown 21 must be supported on an adjacent normal tooth 22 because no assimilation takes place between the jawbone 17 and the artificial dental root of alumina. In order to support the artificial crown 21, the adjacent normal tooth 22 must be partially ground down. Such grinding results in shortening the life of the adjacent normal tooth 22.

Figure 3:
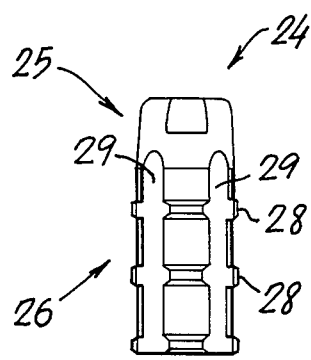
FIG. 3 shows a view of another conventional artificial dental root.
Figure 4:
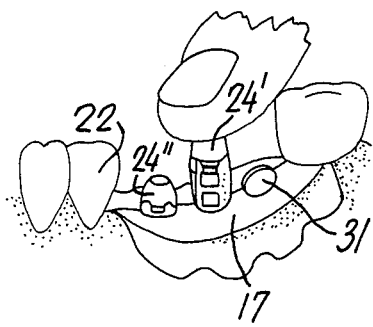
FIG. 4 shows a view for use in describing operation of implanting the conventional artificial dental root illustrated in FIG. 3.

Referring to FIGS. 3 and 4, description will be made as regards another conventional artificial dental root of apatite. The artificial dental root of sintered apatite can be assimilated with a jawbone 17 (FIG. 4) but is weak in mechanical strength as compared with the artificial dental root of alumina illustrated in FIGS. 1 and 2. The illustrated dental root of sintered apatite is therefore greater in diameter than the artificial dental root of alumina and can be clinically applied only to a patient having a wide alveolar bone.

In FIG. 3, the artificial dental root of sintered apatite has a pedestal having upper and lower portions 25 and 26 placed upwards and downwards of FIG. 3, respectively. A pedestal axis is extended through the upper and the lower portions 25 and 26. The upper portion 25 has an upper end directed upwards and is tapered towards the upper end. The lower portion 26 has a cylindrical rod and projections 28 which are protruded from a periphery of the cylindrical rod and which are divided into three partial projections remote from one another along the pedestal axis. The cylindrical rod is chamfered and therefore has chamfered portions 29 spaced apart from one another along the periphery of the cylindrical rod.

With this structure, the projections 28 and the chamfered portions 29 serve to prevent rotation of the pedestal when the lower portion 26 is embedded in the jawbone 17. Accordingly, the projections 28 and the chamfered portions 29 may be called a rotation stopper mechanism.

The artificial dental root of sintered apatite is implanted in the jawbone 17 in a manner illustrated in FIG. 4. More particularly, a hole 31 is formed in the jawbone 17, namely, alveolar bone. The hole 31 must have a diameter slightly smaller than that of the artificial dental root. Otherwise, the artificial dental root might readily be detached from the jawbone 17. Therefore, the dental root is inserted in the hole 31, as depicted at 24' and 24" and is initially fixed to the jawbone 17.

In the meanwhile, it is very difficult to accurately form the above-mentioned hole 31. Accordingly, it takes remarkable skill to form such a hole 31. In addition, such initial fixation is very important and seriously affects the probability of success in surgical operation.

Moreover, the illustrated dental root becomes assimilated with the jawbone 17 after several months and is fixed to the jawbone 17. This means that the artificial crown can not be attached to the dental root for several months until the dental root is fixed to the jawbone 17.

Referring to FIGS. 5 through 7, an artificial dental root according to a first embodiment of this invention comprises a first end 36 directed rightwards of FIG. 5, a second end 37 directed leftwards of FIG. 5 and opposite to the first end 36, and a shank 38 between the first and the second ends 36 and 37. The shank 38 is cylindrical and is about 20 millimeters long. The shank 38 has a shank axis extended through the first and the second ends 36 and 37.

A thread portion 40 is formed around the shank 38 and is specified by a screw thread 41 having a pitch which is not smaller than 2 millimeters. Preferably, the pitch is between 3 millimeters and 4 millimeters.

The second end 37 is embedded in a jawbone while the first end 36 protrudes from the jawbone to be covered with an artificial crown (as will later be described). As shown in FIG. 5, the screw thread 41 is helically extended around an intermediate portion of the shank 38 between the first and the second ends 36 and 37. The thread 41 is wound on the shank 38 over substantially one turn, as shown in FIGS. 5 through 7. The screw thread 41 has a width measured along the shank axis and a height measured radially of the shank 38.

The width and the height of the illustrated screw thread 41 are gradually reduced in size as the screw thread approaches the second end 37. The screw thread 41 is semicircular in cross section.

As shown in FIGS. 5 and 6, a groove 43 is formed on the second end 37 extending transversely of the shank axis. The groove 43 has a depth of about 0.7 millimeter and serves to prevent rotation of the artificial dental root when the dental root is embedded in the jawbone 17. The groove 43 is therefore referred to as a rotation stopper member. Such a rotation stopper member may be either a protrusion projecting from the second end 37 or a combination of a protrusion and a groove.

On the other hand, the shank 38 is partially cut away on the side of the first end 36, as shown in FIG. 5. As a result, the shank 38 has a portion 45 which is tapered towards the first end 36 and which may be called a tapered portion. Thus, the illustrated artificial dental root has a minimum area at the first end 36.

Such a tapered portion 45 serves to readily grasp and rotate the artificial dental root by the use of a pertinent instrument. The tapered portion 45 is formed by chamfering the shank 38 at a portion near the first end 36. Alternatively, the shank 38 may be cut in a frustoconical shape at the portion adjacent to the first end 36.

Referring to FIG. 8, an artificial dental root according to a second embodiment of this invention is similar to that illustrated in FIGS. 5 through 7 except that a single screw thread 41' is trapezoidal in cross section and that a shank 38' has a diameter reduced in size in the direction of the second end 37. The resultant shank 38 is frustoconical in shape and has a peripheral surface inclined at an angle $\theta$, as shown in FIG. 8. Thus, the shank 38 is gradually reduced in diameter as it approaches the second end 37. As in FIGS. 5 through 7, a groove 43 and a tapered portion 45 are formed on the second end 37 and at a portion adjacent to the first end 36, respectively.

Alternatively, a screw thread may be rectangular or triangular in cross section. In this case, it is preferable that corners of the screw thread are rounded. Although the single screw thread is illustrated in FIGS. 5 and 8, a plurality of screw threads may be wound around a shank several turns. At any rate, each of the screw threads may have at least one of a width and a height that is reduced in the direction of the second end 37.

Preferably, each of the aritifical dental roots illustrated in FIGS. 5 and 8 can be manufactured in the following manner. At first, crystalline glass is formed by mixing, by weight, 19.9% of MgO, 28.0% of CaO, 32.0% of $SiO_2$, 15.6% of $P_2O_5$, 4.0% of $ZrO_2$, and 0.5% of $F_2$. The crystalline glass is pulverized into crystallized powder and formed into a body of a dental root shape by pressing, a slip casting, extrusion, or hydrostatic pressing, which may be similar to a method carried out in forming ceramics. The body is subjected to heat treatment to attain glass-ceramics. During the heat treatment, the body is heated at a rate of 3° C./minute to a holding temperature of 1020° C. and is thereafter held at the holding temperature for two hours. As a result, the glass-ceramics have structure wherein apatite, forsterite, and diopside crystals are dispersed in glass matrix. The glass-ceramics have a bending strength of 2100 kg/cm². A large amount of apatite is included in the glass-ceramics. Inasmuch as the apatite is assimilated with the jawbone, as mentioned before, the artificial dental root is assimilated with and strongly fixed to the jawbone when the glass-ceramics are used for the artificial dental root.

Referring to FIG. 9, the artificial dental root illustrated in FIG. 5 is implanted into the jawbone 17 and covered with an artificial crown 21'. As shown in FIG. 9, the artificial crown 21' is not connected to adjacent natural teeth. This means that the artificial dental root illustrated in FIG. 5 is strongly fixed to the jawbone 17 in comparison with the conventional artificial dental root illustrated in FIG. 2. This is because the artificial dental root according to this invention is formly embedded in the jawbone 17 even on initial fixation of the artificial dental root and is strongly received in the jawbone 17 until an os novum grows in a clearance between the artificial dental root and the jawbone 17. In other words, the artificial dental root can be implanted even when the hole for the artificial dental root is not formed with a high precision. Thus, the artificial dental root can be readily attached to the jawbone 17 by simple surgical operation. This applies to the artificial dental root illustrated in FIGS. 5 and 8.

Herein, description will be made about the reason why the artificial dental root is strongly attached to the jawbone 17 on the initial fixation. As illustrated in FIGS. 5 through 7 and FIG. 8, the artificial dental root has the screw thread 41 or 41' having the pitch larger than the conventional one illustrated in FIG. 1. Moreover, the screw thread 41 or 41' has the width and/or height reduced in size as the screw thread 41 or 41' approaches the second end 37.

Such a screw thread 41 or 41' serves to firmly fix the artificial dental root to the jawbone 17. In addition, a large pitch of the screw thread 41 or 41' is helpful to lessen rotation of the artificial dental root on mounting the artificial dental root. Accordingly, it is possible to avoid breakage of a screw thread on the jawbone 17 and to known whether or not the second end 37 of the artificial dental root reaches the bottom of the hole.

Furthermore, the deeper the artificial dental root is embedded into the jawbone 17, the stronger it is fixed to the jawbone 17. This is because the screw thread 41 or 41' is reduced in width and/or height as it approaches the second end 37. Thus, the illustrated dental root is firmly fixed in the hole by the use of resiliency of the jawbone 17.

It is known that involution of the jawbone is objectionably progressive when the stress concentrates on the bottom of the hole. With the screw thread 41 or 41' mentioned above, it is possible to disperse stress not only on the second end 37 but also on a side surface of the artificial dental root because the screw thread 41 or 41' is firmly engaged with the jawbone on the side surface of the artificial dental root. Such involution of the jawbone can therefore be avoided with the artificial screw thread 41 or 41'.

In FIGS. 5 and 8, the groove 43 is formed on the second end 37 and gradually filled with an os novum with time when the artificial dental root is embedded into the jawbone. As a result, rotation of the artificial dental root can be filling of the groove 43 with the os novum. Accordingly, the groove 43 serves to prevent the artificial dental root from being loosened by rotation. Thus, the artificial dental root is firmly engaged with the jawbone 17 even when the artificial dental root is not assimilated with the jawbone 17. This means that the artificial dental root may not comprise apatite. Accordingly, the artificial crown not be connected to an adjacent tooth, as illustrated in FIG. 9, even when no apatite is included in the artificial dental root. As a result, the adjacent tooth is not damaged at all and can keep its life time.

As mentioned before, the artificial dental root is firmly filled even when the hole is opened with a low precision on surgical operation. This makes the operator's or dentist's skill unnecessary. Besides, it is possible with the artificial dental root to increase the probability of success of the surgical operation. Accordingly, the artificial dental root can contribute to wide use of the surgical operation for artificial dental root.

While this invention has thus far been described in conjunction with a few embodiments thereof, it will readily be possible for those skilled in the art to put this invention into practice in various other manners. For example, the artificial dental root may be formed at a portion adjacent to the first end 36 of the shank 38 in various shapes. In addition, the thread portion 40 may be threaded into the shank 38.

What is claimed is:

1. An artificial dental root adapted for insertion into a hole formed in a jawbone, said artificial dental root comprising an elongated tubular body having opposite ends, said tubular body including a first portion extending from one of said ends towards the other of said ends and shaped for insertion into a pre-formed hole provided in a jawbone to serve as a means for anchoring the dental root directly in the jawbone, said tubular body including a second portion extending from the other said end towards said one end to merge with said first portion, said second portion projecting outside the jawbone and serving as a means for attachment of a crown without connecting the crown to adjacent teeth, engaging means on said first portion for resiliently fixing the dental root in the jawbone, said engaging means comprising a thread wound on said body over at least one turn, said thread having a height and width one end closer to said one end of said tubular body at least one of said height and said width being gradually reduced as the screw thread approaches said one end of said tubular body, and continuously increasing in size over the length of the thread in a direction away from said one end towards said other end of said tubular body, said thread having a pitch of at least 2 mm, the shape, size and pitch of said thread enabling insertion of said tubular body into the pre-formed hole in the jawbone with resilient engagement of the dental root and the jawbone.

2. An artificial dental root as claimed in claim 1, wherein said pitch is between 3 millimeters and 4 millimeters.

3. As artificial dental root as claimed in claim 1, wherein said tubular body is gradually reduced in diameter towards said one end thereof.

4. An artificial dental root as claimed in claim 1, comprising rotation stopper means on said one end of said tubular body for stopping rotation of said dental root in the jawbone.

5. An artificial dental root as claimed in claim 4, wherein said rotation stopper means is constituted by a groove formed in said one end of said tubular body.

6. An artificial dental root as claimed in claim 4, wherein said rotation stopper means comprises the combination of a groove and a projection both of which are formed at said one end of the tubular body.

7. An artificial dental root as claimed in claim 1 wherein said thread comprises substantially a single turn on said body.

8. An artificial dental root as claimed in claim 7 wherein the pitch of said thread is sufficiently great in relation to the length of said tubular body to enable the dental root to be inserted into the hole in the jawbone substantially without rotation.

9. An artificial dental root as claimed in claim 7 wherein said thread has a rounded cross-section.

10. An artificial dental root as claimed in claim 1 wherein said one end is flat.

11. An artificial dental root as claimed in claim 1 wherein said dental root is made of a material which will assimilate with the jawbone to become fixed thereto.

12. An artificial dental root as claimed in claim 1 wherein said thread substantially merges with said tubular body at said one end of the thread.

* * * * *